(12) United States Patent
Ko et al.

(10) Patent No.: US 8,193,198 B2
(45) Date of Patent: Jun. 5, 2012

(54) URACIL COMPOUNDS AND A HERBICIDE COMPRISING THE SAME

(75) Inventors: Young Kwan Ko, Daejeon (KR); Kun Hoe Chung, Daejeon (KR); Jae Wook Ryu, Daejeon (KR); Jae Chun Woo, Daejeon (KR); Dong Wan Koo, Daejeon (KR); Dae Whang Kim, Daejeon (KR); Tae Joon Kim, Daejeon (KR); In Young Choi, Daejeon (KR); Young Kwon Kim, Daejeon (KR); Tae Hyun Oh, Daejeon (KR); Jun Hyuk Choi, Daejeon (KR); Mee Young Seok, Daejeon (KR); Kyung Sung Kim, Seoul (KR); Bong Jin Chung, Gwacheon-si (KR)

(73) Assignees: Korea Research Institute of Chemical Technology, Daejeon (KR); Dongbu HiTek Co., Ltd., Seoul (KR)

( * ) Notice: Subject to any disclaimer, the term of this patent is extended or adjusted under 35 U.S.C. 154(b) by 0 days.

(21) Appl. No.: 13/122,199

(22) PCT Filed: Sep. 24, 2009

(86) PCT No.: PCT/KR2009/005471
§ 371 (c)(1),
(2), (4) Date: May 17, 2011

(87) PCT Pub. No.: WO2010/038953
PCT Pub. Date: Apr. 8, 2010

(65) Prior Publication Data
US 2011/0224083 A1  Sep. 15, 2011

(30) Foreign Application Priority Data
Oct. 2, 2008 (KR) .................. 10-2008-0097108

(51) Int. Cl.
A01N 43/54 (2006.01)
C07D 239/42 (2006.01)
C07D 401/04 (2006.01)
(52) U.S. Cl. .................... 514/256; 544/309
(58) Field of Classification Search ............ 544/312, 544/309; 514/256
See application file for complete search history.

(56) References Cited

U.S. PATENT DOCUMENTS

| | | | |
|---|---|---|---|
| 6,403,534 B1 | 6/2002 | Komori et al. | |
| 6,495,491 B1 | 12/2002 | Andree et al. | |
| 2003/0203819 A1* | 10/2003 | Sievernich et al. | 504/138 |

FOREIGN PATENT DOCUMENTS

| | | |
|---|---|---|
| EP | 0255047 | 2/1988 |
| JP | 200-302764 | 10/2000 |
| JP | 2001-172265 | 6/2001 |
| JP | 2001172265 A * | 6/2001 |
| JP | 2008302764 A * | 12/2008 |
| WO | 03/029226 | 4/2006 |
| WO | WO 2008073452 A1 * | 6/2008 |

OTHER PUBLICATIONS

L. M. Abell, Target-Site Directed Herbicide Design, in Pest Control With Enhanced Environmental Safety 16-37 (ACS Symposium Series, vol. 524, 1993).*
M Schlitzer et al., Bioorganic and Medicinal Chemistry, 8(8), 1991-2006 (2000).*
H.H. Weinstock et al., Journal of the American Chemical Society, 62, 3266 (1940).*
Machine translation of O. Itaru et al., JP 2001172265 (Jun. 26, 2001) ("Itaru"). This document was translated at the website of the AIPN Japan Patent Office using the provided web-based translation software ( http://dossier1.ipdl.inpit.go.jp/AIPN/odse_top_dn.ipdl?N0000=7400).*
Machine translation of S. Yuzuru JP 2000302764 (Oct. 31, 2000) ("Yuzuru"). This document was translated at the website of the AIPN Japan Patent Office using the provided web-based translation software ( http://dossier1.ipdl.inpit.go.jp/AIPN/odse_top_dn.ipdl?N0000=7400).*
International Search Report mailed Apr. 26, 2010 for PCT/KR2009/005471.
International Preliminary Report on Patentability for international application No. PCT/KR2009/005471 dated May 10, 2011.

* cited by examiner

*Primary Examiner* — James O Wilson
*Assistant Examiner* — Alexander R Pagano
(74) *Attorney, Agent, or Firm* — Lowe Hauptman Ham & Berner LLP

(57) ABSTRACT

Disclosed are uracil compounds represented by Formula 1, a method for preparing the compounds, and a herbicide including the same as an active ingredient:

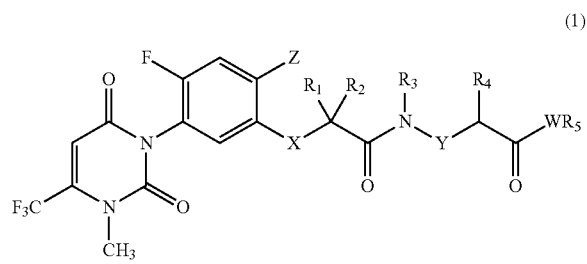

(1)

wherein $R_1$, $R_2$, $R_3$, $R_4$, $R_5$, X, Y, Z and W are the same as defined in the detailed description.

10 Claims, No Drawings

URACIL COMPOUNDS AND A HERBICIDE COMPRISING THE SAME

CROSS REFERENCE TO RELATED APPLICATION

This application claims the priority of Korean Patent Application No. 10-2008-0097108, filed on Oct. 2, 2008, in the KIPO (Korean Intellectual Property Office. Further, this application is the National Phase application of International Application No. PCT/KR2009/005471, filed Sep. 24, 2009, which designates the United States and was published in Korean.

BACKGROUND

1. Field

The present invention relates to novel uracil compounds, a preparation method thereof, and a herbicide comprising the same.

2. Description of the Related Art

Weed control is very important in improving agricultural productivity. A variety of herbicides have been used for the purpose. Triazine-based herbicides such as atrazine or anilide-based herbicides such as alachlor and metolachlor have been used in corn cropping, whereas non-selective herbicides such as paraquat or glyphosate have been used for total vegetative control.

Still, the losses in agriculture due to various kinds of weeds are enormous and thus researches for the development of new herbicides are underway.

With regard to an active substance of a herbicide, Japanese Patent Laid-Open No. 2000-302,764 discloses a compound represented by Formula A.

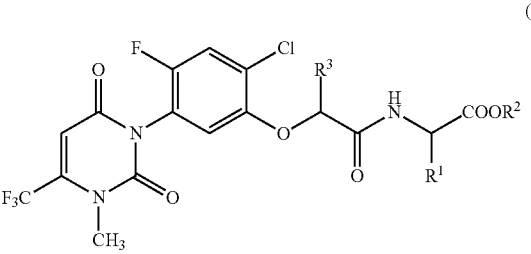

(A)

In Formula A, $R^1$ represents hydrogen or substituted alkyl, $R^2$ represents alkyl, alkenyl or alkynyl, and $R^3$ represents hydrogen or methyl.

Japanese Patent Laid-Open No. 2001-172,265 discloses a compound represented by Formula B.

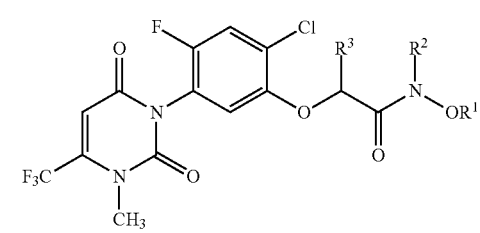

(B)

In Formula B, $R^1$ represents hydrogen or substituted alkyl, $R^2$ represents hydrogen or alkyl, and $R^3$ represents hydrogen or methyl.

And, U.S. Pat. No. 6,403,534 discloses a compound represented by Formula C.

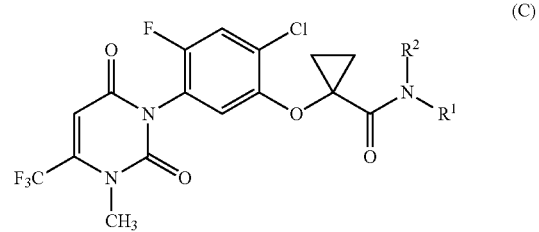

(C)

In Formula C, $R^1$ represents hydrogen, alkyl, haloalkyl, alkenyl or alkynyl, and $R^2$ represents hydrogen, alkyl, haloalkyl, alkenyl, alkynyl, phenyl, benzyl, alkoxy or alkylsulfonyl.

However, the compounds represented by Formula A, B or C need to be used in large quantities when they are used as non-selective herbicides in orchards or non-crop areas. If they are used as selective herbicides, they may harm the desired crop. Therefore, there is an urgent need for the development of highly effective herbicides to solve these problems.

SUMMARY

An object of the present invention is to provide a novel uracil compound and an agrochemically allowable salt thereof.

Another object of the present invention is to provide a herbicide including the uracil compound, the agrochemically allowable salt thereof or a mixture thereof as an active ingredient.

Another object of the present invention is to provide a method for preparing the uracil compound.

The present invention provides a uracil compound represented by Formula 1 or an agrochemically allowable salt thereof:

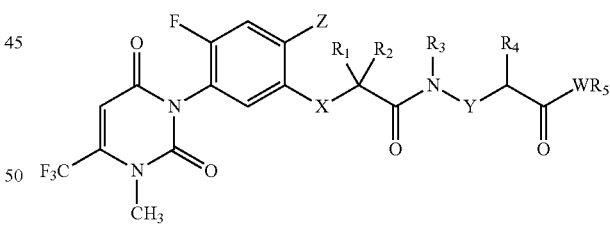

(1)

wherein $R_1$ and $R_2$, which may be the same or different, represent hydrogen or $C_1$-$C_6$ alkyl; $R_3$ represents hydrogen, hydroxyl, $C_1$-$C_6$ alkyl, $C_2$-$C_6$ alkenyl, $C_2$-$C_6$ alkynyl, $C_1$-$C_8$ alkoxy, $C_1$-$C_6$ haloalkyl, $C_2$-$C_6$ haloalkenyl, $C_1$-$C_6$ alkoxy $C_1$-$C_6$ alkyl or $C_6$-$C_{10}$ aryl $C_1$-$C_6$ alkoxy; $R_4$ represents hydrogen, $C_1$-$C_6$ alkyl, $C_1$-$C_6$ haloalkyl or $C_1$-$C_6$ alkoxycarbonyl $C_1$-$C_6$ alkyl; $R_5$ represents hydrogen, $C_1$-$C_6$ alkyl, $C_1$-$C_6$ alkoxy, $C_2$-$C_6$ haloalkyl, $C_2$-$C_6$ alkenyl, $C_2$-$C_6$ haloalkenyl, $C_2$-$C_6$ alkynyl, $C_1$-$C_6$ alkoxycarbonyl $C_1$-$C_6$ alkyl, $C_6$-$C_{10}$ aryl $C_1$-$C_6$ alkyl or $C_6$-$C_{10}$ aryl $C_1$-$C_6$ alkoxy; X represents O, S, SO, $SO_2$, NH or N($C_1$-$C_6$ alkyl); Y represents $C_1$-$C_6$ alkylene or $C_1$-$C_6$ haloalkylene; W represents O, S, NH or N($C_1$-$C_6$ alkyl); and Z represents halogen, cyano, $CONH_2$ or $CSNH_2$.

The uracil compound represented by Formula 1 exhibits a wide herbicidal effect against not only grass weeds but also broadleaf weeds upon foliar treatment at low concentration. Therefore, it is very useful as a non-selective herbicide for foliar treatment in orchards and non-crop areas.

Further, the uracil compound represented by Formula 1 exhibits a good selective herbicidal effect upon soil treatment, with a very superior herbicidal activity against broadleaf and grass weeds without harming useful crops such as wheat or corn. Therefore, the herbicide of the present invention is very useful for use in farmlands, orchards and non-crop areas.

DETAILED DESCRIPTION OF SPECIFIC EMBODIMENTS

The advantages, features and aspects of the invention will become apparent from the following description of the embodiments with reference to the accompanying drawings, which is set forth hereinafter.

In the context of the present invention, the uracil compound represented by Formula 1 includes an agrochemically allowable salt, a racemate, an enantiomer or a diastereoisomer of the compound represented by Formula 1.

The uracil compound represented by Formula 1 may be used in the form of an agrochemically allowable salt. The agrochemically allowable salt may include, for example, a metal salt, a salt with an organic base, a salt with an inorganic acid, a salt with an organic acid, a salt with a basic or acidic amino acid, or the like. A suitable metal salt may include, for example, an alkali metal salt such as sodium salt or potassium salt; an alkaline earth metal salt such as calcium salt, magnesium salt or barium salt; aluminum salt; or the like. The salt with an organic base may include, for example, a salt with trimethylamine, triethylamine, pyridine, picoline, 2,6-lutidine, ethanolamine, diethanolamine, triethanolamine, cyclohexylamine, dicyclohexylamine, N,N-dibenzylethylenediamine, or the like. The salt with an inorganic acid may include, for example, a salt with hydrochloric acid, hydrobromic acid, nitric acid, sulfuric acid, phosphoric acid, or the like. The salt with an organic acid may include, for example, a salt with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, or the like. The salt with a basic amino acid may include, for example, a salt with arginine, lysine, ornithine, or the like. The salt with an acidic amino acid may include, for example, a salt with aspartic acid, glutamic acid, or the like.

Preferably, in the uracil compound represented by Formula 1, $R_1$ and $R_2$, which may be the same or different, represent hydrogen or methyl; $R_3$ represents hydrogen, hydroxyl, methyl, ethyl, n-propyl, isopropyl, n-butyl, tert-butyl, vinyl, allyl, methoxy, ethoxy, n-propoxy, n-butoxy, tert-butoxy, chloromethyl, dichloromethyl, fluoromethyl, difluoromethyl, trifluoromethyl or benzyloxy; $R_4$ represents hydrogen, methyl, ethyl, n-propyl, isopropyl, n-butyl or tert-butyl; $R_5$ represents hydrogen, hydroxyl, methyl, ethyl, n-propyl, isopropyl, n-butyl, tert-butyl, vinyl, allyl, propargyl, methoxy, ethoxy, n-propoxy, n-butoxy, tert-butoxy, benzyl, phenethyl, methoxycarbonylmethyl, methoxycarbonylethyl, methoxycarbonylpropyl, ethoxycarbonylmethyl, benzyloxy or phenethyloxy; X represents O, S, $SO_2$, NH or $N(CH_3)$; Y represents $CH_2$, $CH(CH_3)$, $CH_2CH_2$, $CH_2CH_2CH_2$, $CH(CF_3)$, $CH(CH_2F)$, $CH(CHF_2)$, $CH_2CHF$ or $CH_2CF_2$; W represents O, NH or $N(CH_3)$; and Z represents chlorine, cyano, $CONH_2$ or $CSNH_2$.

More preferably, in the uracil compound represented by Formula 1, $R_1$ and $R_2$, which may be the same or different, represent hydrogen or methyl; $R_3$ represents hydrogen, hydroxyl, methyl, methoxy or benzyloxy; $R_4$ represents hydrogen or methyl; $R_5$ represents hydrogen, methyl, ethyl, n-propyl, n-butyl, methoxy, allyl, propargyl, benzyl, benzyloxy or methoxycarbonylmethyl; X represents O, S, $SO_2$ or NH; Y represents $CH_2$, $CH(CH_3)$, $CH_2CH_2$, $CH_2CH_2CH_2$ or $CH(CH_2F)$; W represents O or NH; and Z represents chlorine, cyano or $CSNH_2$.

More preferably, in the uracil compound represented by Formula 1, $R_1$ and $R_2$, which may be the same or different, represent hydrogen or methyl; $R_3$ represents hydrogen, hydroxyl, methyl or methoxy; $R_4$ represents hydrogen; $R_5$ represents hydrogen, methyl, ethyl, n-butyl, allyl, propargyl or $CH_2CO_2CH_3$; X represents O, S or NH; Y represents $CH_2$, $CH_2CH_2$ or $CH(CH_2F)$; W represents O; and Z represents chlorine.

Specific examples of the uracil compound according to the present invention are given in Table 1.

TABLE 1

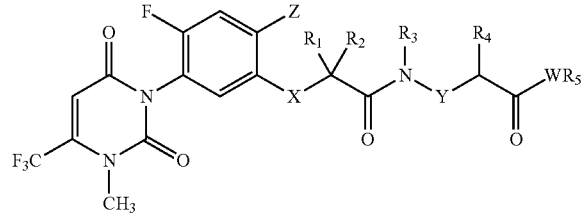

| Comp. No. | $R_1$ | $R_2$ | $R_3$ | $R_4$ | $R_5$ | X | Y | W | Z | $^1$H NMR |
|---|---|---|---|---|---|---|---|---|---|---|
| 1 | Me | H | H | H | Me | O | $CH_2$ | O | Cl | (300 MHz, $CDCl_3$) δ 7.36 (d, 1H, J = 8.8 Hz), 7.17 (br s, 1H), 6.78 (d, 1H, J = 6.3 Hz), 6.37 (s, 1H), 4.63 (q, 1H, J = 6.7 Hz), 3.69 (s, 3H), 3.76-3.47 (m, 5H), 2.56 (t, 2H, J = 5.8 Hz), 1.62 (d, 3H, J = 6.7 Hz) |
| 2 | Me | H | H | Me | Me | O | $CH_2$ | O | Cl | |
| 3 | Me | H | H | H | H | O | $CH_2$ | O | Cl | |
| 4 | Me | H | OMe | H | Me | O | $CH_2$ | O | Cl | (300 MHz, $CDCl_3$) δ 7.32 (d, 1H, J = 8.9 Hz), 6.87 (dd, 1H, $J_1$ = |

TABLE 1-continued

| Comp. No. | $R_1$ | $R_2$ | $R_3$ | $R_4$ | $R_5$ | X | Y | W | Z | $^1$H NMR |
|---|---|---|---|---|---|---|---|---|---|---|
| | | | | | | | | | | 6.5 Hz, $J_2$ = 1.2 Hz), 6.35 (s, 1H), 5.05 (q, 1H, J = 6.6 Hz), 3.95 (m, 2H), 3.66 (m, 6H), 3.55 (d, 3H, J = 7.8 Hz), 2.56 (m, 2H), 1.63 (dd, 3H, $J_1$ = 6.8 Hz, $J_2$ = 1.9 Hz) |
| 5 | Me | H | OBn | H | Me | O | $CH_2$ | O | Cl | (300 MHz, $CDCl_3$) δ 7.37-7.26 (m, 6H), 6.88 (t, 1H, J = 7.7 Hz), 6.36 (d, 1H, J = 1.9 Hz), 4.98 (q, 1H, J = 6.7 Hz), 4.79 (AB q, 2H, J = 10.3 Hz), 4.02 (m, 2H), 3.59 (d, 3H, J = 2.6 Hz), 3.56 (d, 3H, J = 1.0 Hz), 2.57 (m, 2H), 1.56 (m, 3H) |
| 6 | Me | H | OH | H | Me | O | $CH_2$ | O | Cl | (300 MHz, $CDCl_3$) δ 8.33 (d, 1H, J = 17.1 Hz), 7.32 (d, 1H, J = 9.0 Hz), 6.91 (t, 1H, J = 6.8 Hz), 6.35 (d, 1H, J = 5.6 Hz), 5.19 (m, 1H), 4.10-3.76 (m, 2H), 3.69 (s, 3H), 3.57 (d, 3H, J = 1.2 Hz), 2.72 (m, 2H), 1.65 (d, 3H, J = 6.3 Hz) |
| 7 | Me | H | H | H | n-Pr | O | CHMe | O | Cl | |
| 8 | Me | H | H | H | Et | O | $CHCH_2F$ | O | Cl | (300 MHz, $CDCl_3$) δ 7.39-7.24 (m, 2H), 6.81 (d, 1H, J = 6.3 Hz), 6.38 (d, 1H, J = 2.3 Hz), 4.70-4.28 (m, 4H), 4.21-4.10 (m, 2H), 3.57 (d, 3H, J = 4.5 Hz), 2.70 (d, 1H, J = 5.7 Hz), 2.64 (d, 1H, J = 5.2 Hz), 1.64 (d, 1.5H, J = 6.7 Hz), 1.62 (d, 1.5H, J = 6.7 Hz), 1.31-1.20 (m, 3H) |
| 9 | Me | H | H | H | Me | O | CHMe | O | Cl | (300 MHz, $CDCl_3$) δ 7.37 (d, 0.5H, J = 8.8 Hz), 7.36 (d, 0.5H, J = 8.8 Hz), 7.15-7.00 (m, 1H), 6.80 (d, 0.5H, J = 6.3 Hz), 6.70 (d, 0.5H, J = 6.3 Hz), 6.38 (d, 0.5H, J = 3.2 Hz), 6.37 (d, 0.5H, J = 4.1 Hz), 4.60 (m, 1H), 4.35 (m, 1H), 3.71 (s, 1.5H), 3.63 (s, 1.5H), 3.57 (m, 3H), 2.58 (d, 1H, J = 5.6 Hz), 2.50 (d, 1H, J = 5.0 Hz), 1.61 (d, 3H, J = 6.3 Hz), 1.31-1.20 (m, 3H) |
| 10 | Me | H | H | Me | Me | O | $CH_2$ | O | Cl | (300 MHz, $CDCl_3$) δ 7.36 (d, 1H, J = 8.8 Hz), 7.11 (br s, 1H), 6.79 (d, 1H, J = 6.3 Hz), 6.38 (s, 1H), 4.63 (q, 1H, J = 6.7 Hz), 3.67 (d, 3H, J = 2.3 Hz), 3.58 (m, 4H), 3.38 (m, 1H), 2.67 (m, 1H), 1.62 (d, 3H, J = 6.7 Hz), 1.20 (d, 3H, J = 7.2 Hz) |
| 11 | Me | H | H | H | Me | O | $CH_2CH_2$ | O | Cl | (300 MHz, $CDCl_3$) δ 7.36 (d, 1H, J = 8.8 Hz), 6.79 (m, 2H), 6.38 (d, 1H, J = 4.1 Hz), 4.62 (m, 1H), 3.68 (s, 3H), 3.57 (d, 3H, J = 4.5 Hz), 3.36 (q, 2H, J = 6.6 Hz), 2.35 (t, 2H, J = 7.5 Hz), 1.87 (m, 2H), 1.64 (m, 3H) |
| 12 | Me | H | H | H | Me | O | $CH_2CH_2CH_2$ | O | Cl | (300 MHz, $CDCl_3$) δ 7.40 (d, 1H, J = 11.0 Hz), 6.80 (d, 1H, J = 6.3 Hz), 6.70 (br s, 1H), 6.38 (d, 1H, J = 3.7 Hz), δ 4.62 (dq, 1H, $J_1$ = 6.7 Hz, $J_2$ = 2.3 Hz), 3.68 (s, 3H), 3.57 (d, 3H, J = 4.3 Hz), 3.32 (m, 2H), |

TABLE 1-continued

| Comp. No. | R₁ | R₂ | R₃ | R₄ | R₅ | X | Y | W | Z | ¹H NMR |
|---|---|---|---|---|---|---|---|---|---|---|
| | | | | | | | | | | 2.35 (t, 2H, J = 6.9 Hz), 1.60 (m, 7H) |
| 13 | H | H | H | H | Me | O | CH₂ | O | Cl | (300 MHz, CDCl₃) δ 7.38 (d, 1H, J = 8.8 Hz), 7.28 (br s, 1H), 6.79 (d, 1H, J = 6.2 Hz), 6.39 (s, 1H), 4.50 (s, 2H), 3.73 (s, 3H), 3.66 (q, 2H, J = 6.1 Hz), 3.58 (s, 3H), 2.62 (t, 2H, J = 6.0 Hz) |
| 14 | H | H | H | H | H | O | CH₂ | O | Cl | |
| 15 | Me | H | H | H | Me | NH | CH₂ | O | Cl | (200 MHz, CDCl₃) δ 7.26 (d, 1H, J = 9 Hz), 7.05-7.20 (m, 1H), 6.35 (d, 1H, J = 6.2 Hz), 6.32 (s, 1H), 4.45 (br s, 1H), 3.41-3.82 (m, 9H), 2.40-2.58 (m, 2H), 1.54 (d, 3H, J = 7 Hz) |
| 16 | H | H | Me | H | Me | O | CH₂ | O | Cl | (300 MHz, CDCl₃) δ 7.33 (d, 1H, J = 8.8 Hz), 7.01 (d, 0.4H, J = 6.4 Hz), 6.97 (d, 0.6H, J = 6.4 Hz), 6.37 (s, 1H), 4.85 (s, 0.8H), 4.73 (s, 1.2H), 3.77 (t, 0.8H, J = 7.0 Hz), 3.71 (s, 1.2H), 3.67 (s, 1.8H), 3.65 (t, 1.2H, J = 6.9 Hz), 3.57 (s, 3H), 3.15 (s, 1.8H), 2.93 (s, 1.2H), 2.63 (m, 2H) |
| 17 | Me | H | H | H | n-Pr | O | CH₂ | O | Cl | |
| 18 | Me | Me | H | H | Me | O | CH₂ | O | Cl | (200 MHz, CDCl₃) δ 7.40 (br s, 1H), 7.35 (d, 1H, J = 9Hz), 6.90 (d, 1H, J = 6H), 6.35 (s, 1H), 3.68 (s, 3H), 3.55-3.62 (m, 2H), 3.55 (s, 3H), 2.57 (t, 2H, J = 6H), 1.55 (s, 6H) |
| 19 | Me | Me | H | H | Et | O | CH₂ | O | Cl | |
| 20 | Me | H | H | H | Bn | O | CH₂ | O | Cl | (200 MHz, CDCl₃) δ 7.4 (br s, 5H), 7.35 (d, 1H, J = 9 Hz), 7.10-7.25 (br s, 1H), 6.80 (d, 1H, J = 6 Hz), 6.36 (d, 1H, J = 3 Hz), 5.13 (s, 2H), 4.6 (q, 1H, J = 6.7 Hz), 3.55-3.62 (m, 5H), 2.62 (t, 2H, J = 6H), 1.60 (d, 3H, J = 7 Hz) |
| 21 | Me | H | H | H | n-Pr | O | CH₂ | O | Cl | (200 MHz, CDCl₃) δ 7.35 (d, 1H, J = 9 Hz), 7.10-7.25 (m, 1H), 6.79 (d, 1H, J = 6.4 Hz), 6.38 (s, 1H), 4.55-4.70 (m, 1H), 4.05-4.15 (m, 2H), 3.45-3.65 (m, 5H), (2.50-2.62 (m, 2H)), 1.55-1.80 (m, 5H), 0.94 (t, 3H, J = 7.2 Hz) |
| 22 | Me | H | H | H | CH₂CO₂Me | O | CH₂ | O | Cl | (200 MHz, CDCl₃) δ 7.15-7.40 (m, 2H), 6.79 (d, 1H, J = 6.4 Hz), 6.37 (s, 1H), 4.60-4.75 (m, 3H), 3.45-3.80 (m, 8H), 2.66 (t, 2H, J = 5.6 Hz), 1.65 (d, 3H, J = 6.8 Hz) |
| 23 | Me | H | H | H | n-Bu | O | CH₂ | O | Cl | (200 MHz, CDCl₃) δ 7.35 (d, 1H, J = 9 Hz), 7.10-7.25 (m, 1H), 6.79 (d, 1H, J = 6.4 Hz), 6.37 (s, 1H), 4.62 (q, 1H, J = 5.4 Hz), 4.15 (q, 2H, J = 7.4 Hz), 3.45-3.65 (m, 5H), 2.56 (t, 2H, J = 5.6 Hz), 1.25-1.75 (m, 7H), 0.94 (t, 3H, J = 7.2 Hz) |
| 24 | Me | H | H | H | Et | O | CH₂ | O | Cl | (200 MHz, CDCl₃) δ 7.35 (d, 1H, J = 9 Hz), 7.10-7.25 (m, 1H), 6.79 (d, 1H, J = 6.4 Hz), |

TABLE 1-continued

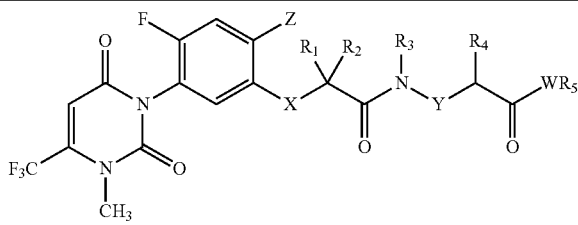

| Comp. No. | R₁ | R₂ | R₃ | R₄ | R₅ | X | Y | W | Z | ¹H NMR |
|---|---|---|---|---|---|---|---|---|---|---|
| | | | | | | | | | | 6.37 (s, 1H), 4.62 (q, 1H, J = 5.4 Hz), 4.15 (q, 2H, J = 7.4 Hz), 3.45-3.65 (m, 5H), 2.56 (t, 2H, J = 5.6 Hz), 1.65 (d, 3H, J = 6.8 Hz), 1.26 (t, 3H, J = 7.4 Hz) |
| 25 | Me | H | H | H | allyl | O | CH₂ | O | Cl | (200 MHz, CDCl₃) δ 7.35 (d, 1H, J = 9 Hz), 7.10-7.25 (m, 1H), 6.79 (d, 1H, J = 6.4 Hz), 6.37 (s, 1H), 5.80-6.00 (m, 1H), 5.25-5.38 (m, 2H), 4.55-4.8 (m, 3H), 3.45-3.65 (m, 5H), 2.59 (t, 2H, J = 5.6 Hz), 1.62 (d, 3H, J = 6.2 Hz) |
| 26 | Me | H | H | H | propargyl | O | CH₂ | O | Cl | (200 MHz, CDCl₃) δ 7.35 (d, 1H, J = 9 Hz), 7.05-7.20 (m, 1H), 6.79 (d, 1H, J = 6.4 Hz), 6.38 (s, 1H), 4.58-4.75 (m, 3H), 3.45-3.70 (m, 5H), 2.62 (t, 2H, J = 5.6 Hz), 2.45-2.50 (m, 1H), 1.62 (d, 3H, J = 5.2 Hz) |
| 27 | Me | Me | H | H | allyl | O | CH₂ | O | Cl | |
| 28 | Me | H | H | H | Et | O | CH₂CH₂ | O | Cl | (300 MHz, CDCl₃) δ 7.36 (d, 1H, J = 8.8 Hz), 6.80 (m, 2H), 6.38 (d, 1H, J = 3.7 Hz), 4.62 (dq, 1H, J₁ = 6.7 Hz, J₂ = 2.0 Hz), 4.14 (q, 2H, J = 7.2 Hz), 3.57 (d, 3H, J = 4.3), 3.36 (q, 2H, J = 6.6 Hz), 2.34 (t, 2H, J = 6.9 Hz), 1.87 (m, 2H), 1.63 (d, 3H, J = 6.7 Hz), 1.27 (t, 3H, J = 7.2 Hz) |
| 29 | Me | H | Me | H | Me | O | CH₂ | O | Cl | |
| 30 | Me | H | Me | H | H | O | CH₂ | O | Cl | |
| 31 | Me | Me | H | H | H | O | CH₂ | O | Cl | |
| 32 | H | H | H | H | Et | O | CH₂ | O | Cl | |
| 33 | Me | H | H | Me | Me | NH | CHMe | O | Cl | |
| 34 | Me | H | CH₂F | H | Me | O | CH₂ | O | Cl | |
| 35 | Me | H | allyl | H | Me | O | CH₂ | O | Cl | |
| 36 | Me | H | H | H | Me | S | CH₂ | O | Cl | (300 MHz, CDCl₃) δ 7.36 (d, 1H, J = 9.0 Hz), 7.24-7.19 (m, 1H), 7.09-6.92 (m, 1H), 6.36 (s, 1H), 3.82 (q, 0.5H, J = 7.3 Hz), 3.81 (q, 0.5H, J = 7.3 Hz), 3.66 (s, 1.5H), 3.65 (s, 1.5H), 3.56 (s, 3H), 3.59-3.40 (m, 2H), 2.46 (t, 2H, J = 6.0 Hz), 1.59 (d, 3H, J = 7.3 Hz) |
| 37 | Me | H | H | H | Et | S | CH₂ | O | Cl | |
| 38 | Me | H | OMe | H | Me | S | CH₂ | O | Cl | |
| 39 | Me | H | H | H | Me | S | CHMe | O | Cl | |
| 40 | Me | H | H | Me | Et | S | CHMe | O | Cl | |
| 41 | Me | H | H | H | Et | O | CHMe | O | Cl | |
| 42 | Me | H | H | H | Me | NH | CH₂ | O | Cl | |
| 43 | Me | H | Me | H | Me | NH | CH₂ | O | Cl | |
| 44 | Me | H | OMe | H | Me | NH | CH₂ | O | Cl | |
| 45 | Me | H | OMe | H | Et | O | CH₂ | O | Cl | |
| 46 | Me | H | H | H | Me | O | CH₂ | O | CN | (300 MHz, CDCl₃) δ 7.42 (d, 1H, J = 8.4 Hz), 6.92 (m, 1H), 6.77 (d, 1H, J = 5.5 Hz), 6.29 (s, 1H), 4.60 (m, 1H), 3.59 (s, 3H), 3.44-3.69 (m, 5H), 2.43-2.48 (m, 2H), 1.57 (d, 3H, J = 6.7 Hz) |
| 47 | Me | H | H | H | Et | O | CH₂ | O | CN | |
| 48 | Me | H | H | H | n-pr | O | CH₂ | O | CN | |
| 49 | Me | H | H | H | Me | O | CH₂ | O | CONH₂ | |

TABLE 1-continued

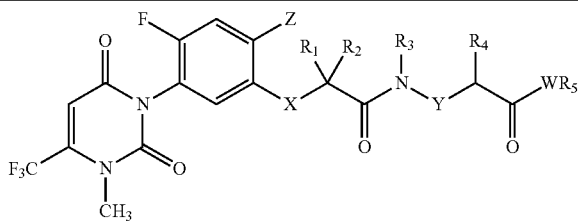

| Comp. No. | R₁ | R₂ | R₃ | R₄ | R₅ | X | Y | W | Z | ¹H NMR |
|---|---|---|---|---|---|---|---|---|---|---|
| 50 | Me | H | H | H | Et | O | CH₂ | O | CONH₂ | |
| 51 | Me | H | H | H | n-pr | O | CH₂ | O | CONH₂ | |
| 52 | Me | H | H | H | Me | O | CH₂ | O | CSNH₂ | (300 MHz, CDCl₃) δ 8.03 (s, 1H), 7.48 (d, 1H, J = 8.4 Hz), 6.98 (s, 1H), 6.85 (m, 1H), 6.82 (m, 1H), 6.38 (d, 1H, J = 5.4 Hz), 4.66 (m, 1H), 3.75 (m, 1H), 3.38 (m, 1H), 2.97 (s, 3H), 2.89 (s, 3H), 2.45-2.59 (m, 2H), 1.66 (d, 3H, J = 6.9 Hz) |
| 53 | Me | H | H | H | Et | O | CH₂ | O | CSNH₂ | |
| 54 | Me | H | H | H | n-pr | O | CH₂ | O | CSNH₂ | |
| 55 | Me | H | H | H | Me | O | CH₂ | NH | Cl | |
| 56 | Me | H | H | H | Et | O | CH₂ | NH | Cl | |
| 57 | Me | H | H | H | OMe | O | CH₂ | NH | Cl | |
| 58 | Me | H | H | H | OH | O | CH₂ | NH | Cl | |
| 59 | Me | H | H | H | OBn | O | CH₂ | NH | Cl | |
| 60 | Me | H | H | H | Me | SO | CH₂ | O | Cl | |
| 61 | Me | H | H | H | Me | SO₂ | CH₂ | O | Cl | (300 MHz, CDCl₃) δ 8.02 (t, 1H, J = 7.4 Hz), 7.48 (d, 1H, J = 9 Hz), 6.94 (m, 1H), 6.36 (s, 1H), 4.41 (q, 1H, J = 5.4 Hz), 3.72 (s, 3H), 3.46-3.56 (m, 5H), 2.52 (m, 2H), 1.57 (m, 3H) |

Me represents methyl, Et represents ethyl, n-Pr represents propyl, n-Bu represents butyl, and Bn represents benzyl.

Of the examples of the uracil compounds represented by Formula 1 given in Table 1, particularly preferable compounds are as follows:

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid methyl ester (Compound No. 1);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}methoxyamino]propionic acid methyl ester (Compound No. 4);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}benzyloxyamino]propionic acid methyl ester (Compound No. 5);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}hydroxyamino]propionic acid methyl ester (Compound No. 6);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]-4-fluorobutyric acid methyl ester (Compound No. 8);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]butyric acid methyl ester (Compound No. 9);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]-2-methylpropionic acid methyl ester (Compound No. 10);

4-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]butyric acid methyl ester (Compound No. 11);

5-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]pentanoic acid methyl ester (Compound No. 12);

3-[{2-[2-chloro-5-(3,6-dihydro-3-methyl-2,6-dioxo-4-trifluoromethyl-1(2H)-pyrimidinyl)-4-fluorophenoxy]-1-oxoethyl}amino]propionic acid methyl ester (Compound No. 13);

3-[{2-[2-chloro-5-(3,6-dihydro-3-methyl-2,6-dioxo-4-trifluoromethyl-1(2H)-pyrimidinyl)-4-fluorophenylamino]-1-oxopropyl}amino]propionic acid methyl ester (Compound No. 15);

3-[{2-[2-chloro-5-(3,6-dihydro-3-methyl-2,6-dioxo-4-trifluoromethyl-1(2H)-pyrimidinyl)-4-fluorophenoxy]-1-oxoethyl}methylamino]propionic acid methyl ester (Compound No. 16);

3-[{2-[2-chloro-5-(3,6-dihydro-3-methyl-2,6-dioxo-4-trifluoromethyl-1(2H)-pyrimidinyl)-4-fluorophenoxy]-1-oxoisobutyl}amino]propionic acid methyl ester (Compound No. 18);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid benzyl ester (Compound No. 20);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid n-propyl ester (Compound No. 21);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionyloxy acetic acid methyl ester (Compound No. 22);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid n-butyl ester (Compound No. 23);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid ethyl ester (Compound No. 24);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid allyl ester (Compound No. 25);

3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid propargyl ester (Compound No. 26);

4-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]butyric acid ethyl ester (Compound No. 28);

3-[{2-[2-chloro-5-(3,6-dihydro-3-methyl-2,6-dioxo-4-trifluoromethyl-1(2H)-pyrimidinyl)-4-fluorophenylthio]-1-oxopropyl}amino]propionic acid methyl ester (Compound No. 36);

3-[{2-[2-cyano-5-(3,6-dihydro-3-methyl-2,6-dioxo-4-trifluoromethyl-1(2H)-pyrimidinyl)-4-fluorophenoxy]-1-oxopropyl}amino]propionic acid methyl ester (Compound No. 46);

3-[{2-[2-aminothiocarbonyl-5-(3,6-dihydro-3-methyl-2,6-dioxo-4-trifluoromethyl-1(2H)-pyrimidinyl)-4-fluorophenoxy]-1-oxopropyl}amino]propionic acid methyl ester (Compound No. 52); and 3-[{2-[2-chloro-5-(3,6-dihydro-3-methyl-2,6-dioxo-4-trifluoromethyl-1(2H)-pyrimidinyl)-4-fluorophenylsulfonyl]-1-oxopropyl}amino]propionic acid methyl ester (Compound No. 61).

The present invention also provides a method for preparing the uracil compound represented by Formula 1.

A first method for preparing the uracil compound represented by Formula 1 according to the present invention comprises, as shown in Scheme 1, reacting a carboxylic acid compound represented by Formula 2 with a chlorinating reagent to prepare a carboxylic acid chloride, and reacting the resultant carboxylic acid chloride with an amino acid ester compound represented by Formula 3 to obtain the desired uracil compound:

In the preparation method of Scheme 1, the carboxylic acid compound (Z=Cl) represented by Formula 2 is a known compound disclosed in WO 03/029226 and Japanese Patent Laid-Open No. 2000-302764. The amino acid ester compound represented by Formula 3 is commercially available or known or may be easily prepared by those skilled in the art using known methods.

The chlorinating reagent used in Scheme 1 may be a commonly used chlorinating reagent. Specifically, thionyl chloride, phosgene, phosphoryl oxychloride, oxalyl chloride, phosphorus trichloride, phosphorus pentachloride, or the like may be used. The chlorination reaction may be carried out in a solvent or without a solvent. When the chlorination reaction is carried out in a solvent, the reaction solvent may be any organic solvent commonly used in the art. Specifically, dichloromethane, chloroform, dichloroethane, ethyl acetate, cyclohexane, benzene, chlorobenzene, toluene, tetrahydrofuran, diisopropyl ether, 1,4-dioxane, or the like may be used. Preferably, the chlorinating reagent is used in excess of 1 mol per 1 mol of the carboxylic acid compound represented by Formula 2, and the reaction is performed at 20° C. to 150° C.

When the chlorination reaction is completed, the reaction mixture is concentrated under reduced pressure, dissolved in a solvent and reacted with the amino acid ester compound represented by Formula 3. Preferably, the reaction is carried out under a basic condition. An organic base such as triethylamine, pyridine, dimethylaniline, etc. or an inorganic base such as $Na_2CO_3$, $K_2CO_3$, $Li_2CO_3$, etc., may be used. Preferably, the reaction temperature is 0° C. to 100° C. The quantity of the amino acid ester compound represented by Formula 3 used may depend on whether a base is used or not. Under a reaction condition where a base is not used, it is preferred that 2 mol or more of the amino acid ester compound represented by Formula 3 is used per 1 mol of the carboxylic acid compound. And, under a reaction condition where a base is used, it is preferred that 1 mol or more of the amino acid ester compound represented by Formula 3 and 1 mol or more of a base is used per 1 mol of the carboxylic acid compound. After the reaction is completed, the reaction mixture is diluted with an organic solvent and washed with an acid. Thus obtained organic layer is dried, concentrated and purified by column chromatography.

A second method for preparing the uracil compound represented by Formula 1 according to the present invention comprises, as shown in Scheme 2, amide coupling reaction of a carboxylic acid compound represented by Formula 2 and an amino acid ester compound represented by Formula 3 using a dehydrating agent to directly obtain the desired uracil compound:

Scheme 1

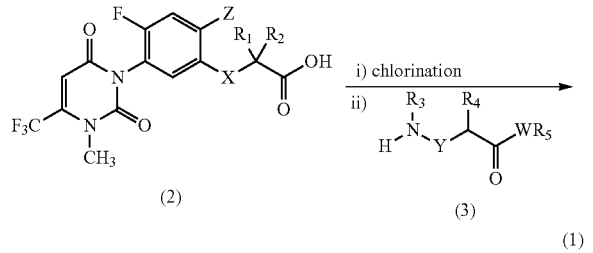

(1)

In Scheme 1, $R_1$, $R_2$, $R_3$, $R_4$, $R_5$, X, Y, Z and W are the same as defined in Formula 1.

Scheme 2

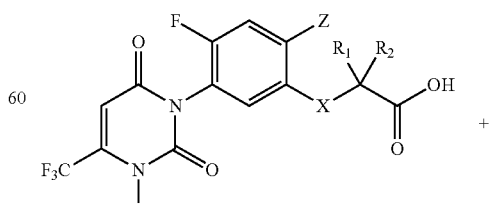

(2)

-continued

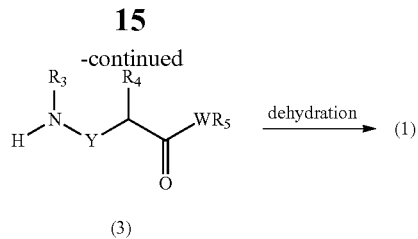

(3)

In Scheme 2, $R_1, R_2, R_3, R_4, R_5, X, Y, Z$ and W are the same as defined in Formula 1.

The dehydrating agent used in Scheme 2 may be a dehydrating agent commonly used in amide coupling reaction. It may be selected from N,N-carbonyldiimidazole, N,N-cyclohexyl carbodiimide, N-(3-dimethylaminopropyl)-N'-ethylcarbodiimide and (benzotriazol-1-yl)-N,N,N',N'-tetramethyluronium tetrafluoroborate, but is not limited thereto. The dehydrating agent may be used in an amount of 1 to 1.5 mol per 1 mol of the carboxylic acid compound represented by Formula 2. If necessary, N,N-dimethylaminopyridine may be used in the dehydration as a catalyst. The catalyst may be used in an amount of 0.05 to 0.1 mol per 1 mol of the carboxylic acid compound represented by Formula 2. The dehydration may be performed in a temperature range of 0° C. to 80° C., preferably 20° C. to 50° C. For a reaction solvent, an organic solvent commonly used in the art may be used. Specifically, dichloromethane, dichloroethane, ethyl acetate, acetonitrile, toluene, tetrahydrofuran, diethyl ether, dimethyl formamide, or the like may be used. After the reaction is completed, the reaction mixture may be purified by an usual separation process. For example, the reaction mixture may be diluted with an organic solvent and washed with an acidic aqueous solution, and then the organic layer may be concentrated under reduced pressure. If required, it may be purified by column chromatography.

A third method for preparing the uracil compound represented by Formula 1 according to the present invention comprises, as shown in Scheme 3, nucleophilically substituting a compound represented by Formula 4 with a compound represented by Formula 5 under a basic condition.

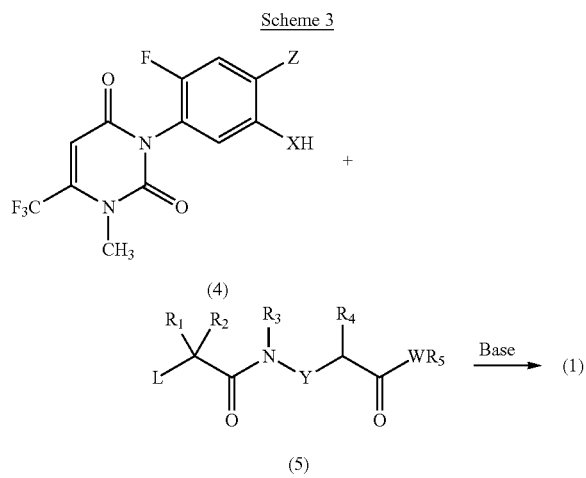

In Scheme 3, $R_1, R_2, R_3, R_4, R_5, X, Y, Z$ and W are the same as defined in Formula 1, L represents a leaving group, which may be methanesulfonate (—OMs), p-toluenesulfonate (—OTs), halogen (e.g., Cl, Br), or the like.

In the nucleophilic substitution reaction according to Scheme 3, any organic solvent commonly used in the art may be used as a reaction solvent. Specifically, dichloromethane, chloroform, dichloroethane, ethyl acetate, cyclohexane, benzene, chlorobenzene, toluene, cyclohexane, tetrahydrofuran, diisopropyl ether, 1,4-dioxane and acetonitrile, or the like may be used. And, an organic base such as triethylamine, pyridine, dimethylaniline, etc. or an inorganic base such as $NaHCO_3$, $KHCO_3$, $Na_2CO_3$, $K_2CO_3$, $Li_2CO_3$, etc. may be used as a base in the nucleophilic substitution. Preferably, the base is used in an amount of 1 to 1.1 mol per 1 mol of the compound represented by Formula 5. The nucleophilic substitution reaction is performed in a temperature range of 0° C. to 100° C.

The compound represented by Formula 4 is a known compound. Specifically, a compound with Z=Cl and X=O has a CAS registry number 114136-60-6 and is disclosed in U.S. Pat. No. 6,537,948, a compound with Z=Cl and X=S has a CAS registry number 353292-92-9 and is disclosed in U.S. Pat. No. 6,537,948, a compound with Z=Cl and X=NH has a CAS registry number 114136-76-4 and is disclosed in U.S. Pat. No. 4,859,229, and a compound with Z=CN and X=O has a CAS registry number 367253-28-9 and is disclosed in European Patent No. 1,272,478.

The compound represented by Formula 5 may be prepared according to Scheme 4 and Scheme 5.

According to Scheme 4, a carboxylic acid compound represented by Formula 6 is chlorinated by a common method using a chlorinating reagent, and the product is reacted with an amino acid ester compound represented by Formula 3 to prepare the compound represented by Formula 5.

Scheme 4

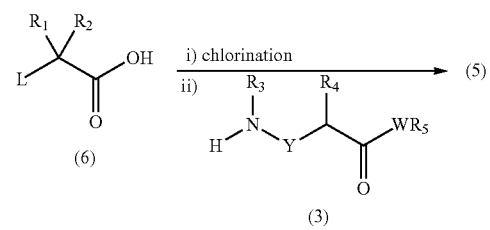

In Scheme 4, $R_1, R_2, R_3, R_4, R_5, Y$ and W are the same as defined in Formula 1, and L represents a leaving group, which may be methanesulfonate (—OMs), p-toluenesulfonate (—OTs), halogen (e.g., Cl, Br), or the like.

Some of the amino acid ester compound represented by Formula 3 and the carboxylic acid compound represented by Formula 6 are known, and some of them are commercially available. Also, the compounds may be easily prepared by those skilled in the art according to the method known in the literature.

In Scheme 4, the chlorinating reagent may be selected from the reagent used in the chlorination reaction according to Scheme 1, and is preferably used in excess of 1 mol per 1 mol of the carboxylic acid compound represented by Formula 6. The reaction is performed in a temperature range of 20° C. to 150° C.

After the chlorination is completed, the reaction mixture is concentrated under reduced pressure, dissolved in a solvent, and then reacted with the amino acid ester compound represented by Formula 3. Preferably, the reaction is performed under a basic condition. An organic base such as triethylamine, pyridine, dimethylaniline, etc. or an inorganic base such as $Na_2CO_3$, $K_2CO_3$, $Li_2CO_3$, etc. may be used. Preferably, the reaction temperature is 0° C. to 100° C. The quantity of the amino acid ester compound represented by Formula 3 used may depend on whether a base is used or not. Under a reaction condition where a base is not used, it is preferred that 2 mol or more of the amino acid ester compound represented by Formula 3 is used per 1 mol of the carboxylic acid compound. And, under a reaction condition where a base is used, it is preferred that 1 mol or more of the amino acid ester compound represented by Formula 3 and 1 mol or more of a base is used per 1 mol of the carboxylic acid compound. After the reaction is completed, the reaction mixture is diluted with an organic solvent and washed with an acid. Thus obtained organic layer is dried, concentrated and purified by column chromatography.

Another method for preparing the compound represented by Formula 5 comprises, as shown in Scheme 5, amide coupling reaction of a carboxylic acid compound represented by Formula 6 and an amino acid ester compound represented by Formula 3 using a dehydrating agent.

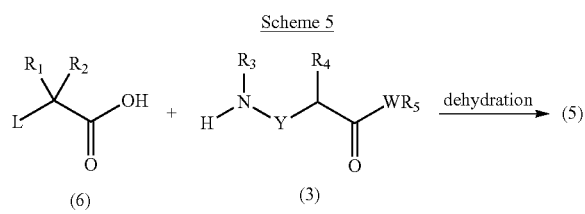

In Scheme 5, $R_1$, $R_2$, $R_3$, $R_4$, $R_5$, Y and W are the same as defined in Formula 1, and L represents a leaving group, which may be methanesulfonate (—OMs), p-toluenesulfonate (—OTs), halogen (e.g., Cl, Br), or the like.

The dehydrating agent used in Scheme 5 may be a dehydrating agent commonly used in amide coupling reaction. It may be selected from N,N-carbonyldiimidazole, N,N-cyclohexyl carbodiimide, N-(3-dimethylaminopropyl)-N'-ethylcarbodiimide and (benzotriazol-1-yl)-N,N,N',N'-tetramethyluronium tetrafluoroborate, but is not limited thereto. The dehydrating agent may be used in an amount of 1 to 1.5 mol per 1 mol of the carboxylic acid compound represented by Formula 6. If necessary, N,N-dimethylaminopyridine may be used in the dehydration reaction as a catalyst. The catalyst may be used in an amount of 0.05 to 0.1 mol per 1 mol of the carboxylic acid compound represented by Formula 6. The dehydration reaction may be performed in a temperature range of 0° C. to 80° C., preferably 20° C. to 50° C. For a reaction solvent, an organic solvent commonly used in the art may be used. Specifically, dichloromethane, dichloroethane, ethyl acetate, acetonitrile, toluene, tetrahydrofuran, diethyl ether, dimethyl formamide, or the like may be used. After the reaction is completed, the reaction mixture may be purified by an usual separation process. For example, the reaction mixture may be diluted with an organic solvent and washed with an acidic aqueous solution, and then the organic layer may be concentrated under reduced pressure. If required, it may be purified by column chromatography.

And, of the compound of the present invention, a uracil compound represented by Formula 1b, with X=SO or $SO_2$, may be prepared by, as shown in Scheme 6, oxidizing a uracil compound represented by Formula 1a with X=S.

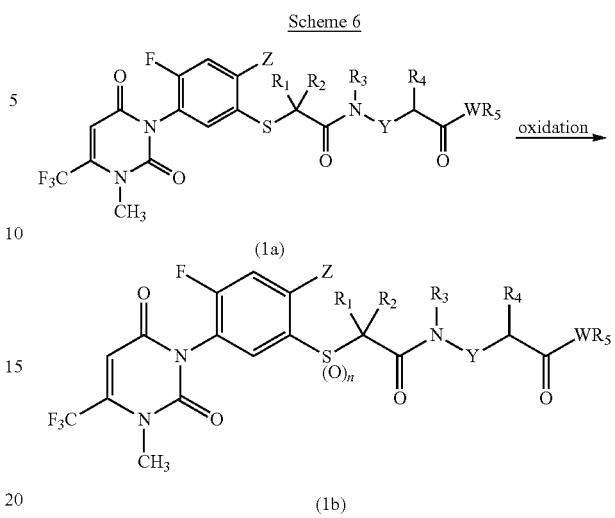

In Scheme 6, $R_1$, $R_2$, $R_3$, $R_4$, $R_5$, Y, Z and W are the same as defined in Formula 1, and n, which represents the number of oxygen (O) atoms, is an integer 1 or 2.

The oxidation according to Scheme 6 may be carried out using the method disclosed in the literature *Phosphorus, Sulfur and Silicon and the Related Elements*; English; 45; 1989; 31-34; *Synthesis*; English; 7; 1997; 787-791. In the present invention, Oxone, MCPBA, $H_2O_2$, $KMnO_4$, $NaIO_4$, t-BuOCl, $Ca(OCl)_2$, $NaClO_2$, sodium hypochlorite (NaOCl), dioxirane, nitric acid ($HNO_3$), ceric ammonium nitrate, or the like may be used as an oxidizing agent.

And, of the compound of the present invention, a uracil compound represented by Formula 1d, with Z=$CONH_2$, may be prepared, as shown in Scheme 7, by the method disclosed in the literature *Journal of Chemical Research*, Miniprint; English; 12; 1985; 3830-3860 using a uracil compound represented by Formula 1c with Z=CN as a starting material.

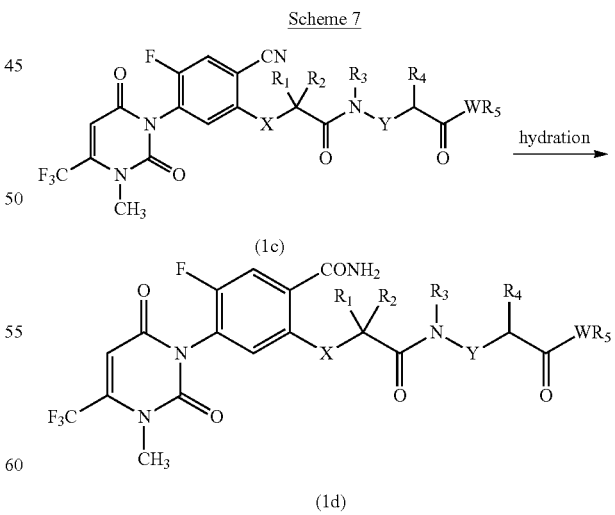

In Scheme 7, $R_1$, $R_2$, $R_3$, $R_4$, $R_5$, X, Y and W are the same as defined in Formula 1.

And, of the compound of the present invention, a uracil compound represented by Formula 1e, with Z=$CSNH_2$, may be prepared, as shown in Scheme 8, by the method disclosed in the literature *Phosphorus, Sulfur and Silicon and the Related Elements*; English; 25; 1985; 297-306 using a uracil compound represented by Formula 1c with Z=CN as a starting material.

Scheme 8

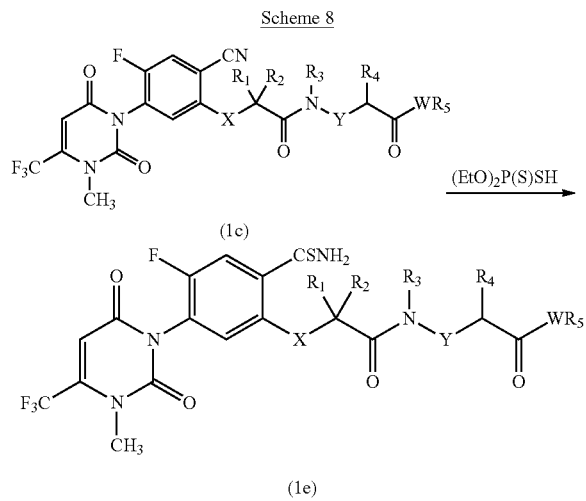

(1c)

(1e)

In Scheme 8, $R_1$, $R_2$, $R_3$, $R_4$, $R_5$, X, Y and W are the same as defined in Formula 1.

EXAMPLES

The examples (and experiments) will now be described. The following examples (and experiments) are for illustrative purposes only and not intended to limit the scope of this disclosure.

Preparation Example 1

Synthesis of 2-chloropropionyl chloride

Thionyl chloride ($SOCl_2$, 17.8 g) was added dropwise at 50° C. for 30 minutes to a solution of 2-chloropropionic acid (10.8 g) in dimethylformamide (0.5 mL). After stirring for 7 hours at the same temperature, the reaction mixture was distilled at 112° C. to give pale-yellow oil (9.4 g).

$^1$H NMR ($CDCl_3$, 300 MHz) δ 4.68 (q, 1H, J=7.0 Hz), 1.84 (d, 3H, J=7.0 Hz).

Preparation Example 2

Synthesis of 3-(2-chloropropionylamino)propionic acid methyl ester

Triethylamine (1.63 g) was added to a suspension of β-alanine methyl ester hydrochloride (2.25 g) in dichloromethane (10 mL) and the reaction mixture was stirred for 30 minutes. After addition of pyridine (1.27 g) the reaction mixture was cooled to 0° C. A solution of 2-chloropropionyl chloride (2.04 g) in dichloromethane (10 mL) was added dropwise for 20 minutes. The reaction mixture was stirred for 2 hours, washed sequentially with water, 1 N hydrochloric acid and saturated sodium bicarbonate, dried with magnesium sulfate, filtered, and concentrated to give yellow oil (2.9 g, yield 93%).

$^1$H NMR ($CDCl_3$, 300 MHz) δ 7.15 (br s, 1H), 4.41 (q, 1H, J=7.0 Hz), 3.74 (s, 3H), 3.58 (q, 2H, J=6.1 Hz), 2.59 (t, 2H, J=6.0 Hz), 1.74 (d, 3H, J=7.1 Hz).

Example 1

Synthesis of 3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid methyl ester (Compound No. 1)

2-[2-Chloro-5-(3,6-dihydro-3-methyl-2,6-dioxo-4-trifluoromethyl-1(2H)-pyrimidinyl)-4-fluorophenoxy]propionic acid (20 g) and β-alanine methyl ester hydrochloride (8.2 g) were dissolved in dichloromethane (200 mL). After slowly adding 4-methylmorpholine (14.8 g) dropwise to the reaction mixture, stirring was performed for 1 hour. After adding (benzotriazol-1-yl)-N,N,N',N'-tetramethyluronium tetrafluoroborate (18.5 g) for 30 minutes, the reaction mixture was stirred at room temperature for 1.5 hours. The reaction mixture was washed with water, dried with magnesium sulfate and concentrated. The concentrate was purified by silica gel column chromatography to give the target compound (24 g) including a trace amount of impurities, which was recrystallized twice using a mixture solvent of ethyl acetate and hexane to give the target compound (18.2 g).

$^1$H NMR ($CDCl_3$) δ 7.36 (d, 1H, J=8.8 Hz), 7.17 (br s, 1H), 6.78 (d, 1H, J=6.3 Hz), 6.37 (s, 1H), 4.63 (q, 1H, J=6.7 Hz), 3.69 (s, 3H), 3.76-3.47 (m, 5H), 2.56 (t, 2H, J=5.8 Hz), 1.62 (d, 3H, J=6.7 Hz).

Example 2

Synthesis of 3-[{2-[2-chloro-5-(3,6-dihydro-3-methyl-2,6-dioxo-4-trifluoromethyl-1(2H)-pyrimidinyl)-4-fluorophenoxy]-1-oxopropyl}amino]propionic acid methyl ester (Compound No. 1)

Oxalyl chloride (2 mL) was added dropwise to 2-[2-chloro-5-(3,6-dihydro-3-methyl-2,6-dioxo-4-trifluoromethyl-1(2H)-pyrimidinyl)-4-fluorophenoxy]propionic acid (1.00 g). After stirring the reaction mixture at room temperature for 1 hour, followed by concentration under reduced pressure, acid chloride (1.00 g) was obtained. Thus obtained acid chloride was dissolved in dichloromethane (10 mL), and after cooling to 0° C., triethylamine (0.70 mL) and β-alanine methyl ester hydrochloride (357 mg) were sequentially and slowly added dropwise. The reaction mixture was stirred at 5° C. or below for 2 hours, washed with water, dried with magnesium sulfate and concentrated. The concentrate was purified by silica gel column chromatography to give the target compound (800 mg).

$^1$H NMR ($CDCl_3$) δ 7.36 (d, 1H, J=8.8 Hz), 7.17 (br s, 1H), 6.78 (d, 1H J=6.3 Hz), 6.37 (s, 1H), 4.63 (q, 1H, J=6.7 Hz), 3.69 (s, 3H), 3.76-3.47 (m, 5H), 2.56 (t, 2H, J=5.8 Hz), 1.62 (d, 3H, J=6.7 Hz).

Example 3

Synthesis of 3-[{2-[2-chloro-5-(3,6-dihydro-3-methyl-2,6-dioxo-4-trifluoromethyl-1(2H)-pyrimidinyl)-4-fluorophenoxy]-1-oxopropyl}methoxyamino]propionic acid methyl ester (Compound No. 4)

2-[2-chloro-5-(3,6-dihydro-3-methyl-2,6-dioxo-4-trifluoromethyl-1(2H)-pyrimidinyl)-4-fluorophenoxy]propionic acid (200 mg) and methyl 3-(methoxyamine)propanoate (66 mg) were dissolved in dichloromethane (2 mL). 4-Methylmorpholine (162 μL) was slowly added dropwise to the reaction mixture, and stirred for 30 minutes. After adding (benzotriazol-1-yl)-N,N,N',N'-tetramethyluronium tetrafluoroborate (186 mg) for 30 minutes, the reaction mixture was stirred at room temperature for 3 hours and 30 minutes. The reaction mixture was washed with water, dried with magnesium sulfate and concentrated. The concentrate was purified by silica gel column chromatography to give the target compound (170 mg).

$^1$H NMR (CDCl$_3$) δ 7.32 (d, 1H, J=8.9 Hz), 6.87 (dd, 1H, J$_1$=6.5 Hz, J$_2$=1.2 Hz), 6.35 (s, 1H), 5.05 (q, 1H, J=6.6 Hz), 3.95 (m, 2H), 3.66 (m, 6H), 3.55 (d, 3H, J=7.8 Hz), 2.56 (m, 2H), 1.63 (dd, 3H, J$_1$=6.8 Hz, J$_2$=1.9 Hz).

Example 4

Synthesis of 3-[{2-[2-chloro-5-(3,6-dihydro-3-methyl-2,6-dioxo-4-trifluoromethyl-1(2H)-pyrimidinyl)-4-fluorophenoxy]-1-oxoethyl}amino]propionic acid methyl ester (Compound No. 13)

[2-Chloro-5-(3,6-dihydro-3-methyl-2,6-dioxo-4-trifluoromethyl-1(2H)-pyrimidinyl)-4-fluoro]phenoxyacetic acid (100 mg) and β-alanine methyl ester hydrochloride (43 mg) were suspended in dichloromethane (1 mL). 4-Methylmorpholine (100 μL) was slowly added dropwise to the reaction mixture and (benzotriazol-1-yl)-N,N,N',N'-tetramethyluronium tetrafluoroborate (97 mg) was added for 1 hour. After stirring at room temperature for 3 hours, the reaction mixture was washed with water, dried with magnesium sulfate and concentrated. The concentrate was purified by silica gel column chromatography to give the target compound (96 mg).

$^1$H NMR (CDCl$_3$) δ 7.38 (d, 1H, J=8.8 Hz), 7.28 (br s, 1H), 6.79 (d, 1H, J=6.2 Hz), 6.39 (s, 1H), 4.50 (s, 2H), 3.73 (s, 3H), 3.66 (q, 2H, J=6.1 Hz), 3.58 (s, 3H), 2.62 (t, 2H, J=6.0 Hz).

Example 5

Synthesis of 3-[{2-[2-chloro-5-(3,6-dihydro-3-methyl-2,6-dioxo-4-trifluoromethyl-1(2H)-pyrimidinyl)-4-fluorophenylamino]-1-oxopropyl}amino]propionic acid methyl ester (Compound No. 15)

3-[2-(Toluene-4-sulfonyloxy)-propionylamino]propionic acid methyl ester (307 mg) was dissolved in acetonitrile (5 mL). After addition of 1-methyl-3-(5-amino-4-chloro-2-fluorophenyl)-6-trifluoromethyl-1H-pyrimidin-2,4-dione (300 mg) and potassium carbonate (135 mg), the reaction mixture was heated for 6 hours under reflux without cooling. After cooling to room temperature, the reaction mixture was diluted with ethyl acetate (50 mL) and washed with water (50 mL). Thus obtained organic layer was dried with magnesium sulfate and concentrated. The concentrate was purified by silica gel column chromatography to give the target compound (170 mg).

$^1$H NMR (CDCl) δ 7.26 (d, 1H, J=9 Hz), 7.05-7.20 (m, 1H), 6.35 (d, 1H, J=3.2 Hz), 6.32 (s, 1H), 4.45 (br s, 1H), 3.41-3.82 (m, 9H), 2.40-2.58 (m, 2H), 1.54 (d, 3H, J=7 Hz).

Example 6

Synthesis of 3-[{2-[2-chloro-5-(3,6-dihydro-3-methyl-2,6-dioxo-4-trifluoromethyl-1(2H)-pyrimidinyl)-4-fluorophenoxy]-1-oxoisobutyl}amino]propionic acid methyl ester (Compound No. 18)

3-(2-Bromo-2-methylpropionylamino)propionic acid methyl ester (224 mg) and 3-(4-chloro-2-fluoro-5-hydroxyphenyl)-1-methyl-6-trifluoromethyl-1H-pyrimidin-2,4-dione (250 mg) were dissolved in acetonitrile 5 ml. After addition of K$_2$CO$_3$ (204 mg), the reaction mixture was heated for 12 hours under reflux, cooled and diluted with ethyl acetate (50 mL). After washing with water (50 mL), thus obtained organic layer was dried with magnesium sulfate and concentrated. The concentrate was purified by silica gel column chromatography to give the target compound (240 mg).

$^1$H NMR (CDCl$_3$) δ 7.40 (br s, 1H), 7.35 (d, 1H, J=9 Hz), 6.90 (d, 1H, J=6 Hz), 6.35 (s, 1H), 3.68 (s, 3H), 3.55-3.62 (m, 2H), 3.55 (s, 3H), 2.57 (t, 2H, J=6 Hz), 1.55 (s, 6H), 1.43 (s, 3H).

Example 7

Synthesis of 3-[{2-[2-chloro-5-(3,6-dihydro-3-methyl-2,6-dioxo-4-trifluoromethyl-1(2H)-pyrimidinyl)-4-fluorophenylthio]-1-oxopropyl}amino]propionic acid methyl ester (Compound No. 36)

To a suspension of 3-(2-chloropropionylamino)propionic acid methyl ester (6.93 g) and potassium carbonate (4.72 g) in acetonitrile (150 mL) was added dropwise a solution of 3-(4-chloro-2-fluoro-5-mercaptophenyl)-1-methyl-6-trifluoromethyl-1H-pyrimidin-2,4-dione (11.54 g) in acetonitrile (75 mL) at 45° C. to 50° C. for 1 hour. The reaction mixture was stirred at the same temperature for 2 hours and neutralized at 5° C. with 1 N hydrochloric acid. Water and ethyl acetate were added to separate the organic layer. The aqueous layer was extracted with ethyl acetate. The combined organic layer was washed with brine, dried with magnesium sulfate, filtered, concentrated, and recrystallized with ether to give the target compound (13.00 g, yield 78%, white solid).

$^1$H NMR (CDCl$_3$, 300 MHz) δ 7.36 (d, 1H, J=9.0 Hz), 7.24-7.19 (m, 1H), 7.09-6.92 (m, 1H), 6.36 (s, 1H), 3.82 (q, 0.5H, J=7.3 Hz), 3.81 (q, 0.5H, J=7.3 Hz), 3.66 (s, 1.5H), 3.65 (s, 1.5H), 3.56 (s, 3H), 3.59-3.40 (m, 2H), 2.46 (t, 2H, J=6.0 Hz), 1.59 (d, 3H, J=7.3 Hz).

FORMULATION EXAMPLES

The uracil compound represented by Formula 1 is useful as a herbicide. When used as a herbicide, an additive commonly used in the preparation of agrichemicals such as diluent, surfactant, dispersant or adjuvant may be mixed with the compound represented by Formula 1 to prepare various types of formulations, including wettable powder, emulsifiable concentrate, wettable powder, soluble concentrate, or the like. These formulations may be used directly or as diluted with an adequate medium. A spray volume of the herbicide may be hundreds to thousands liters per hectare (ha).

A herbicidal composition according to the present invention comprises 0.1 wt % to 99.9 wt % of the uracil compound represented by Formula 1, an agrochemically allowable salt thereof or a mixture thereof and 0.1 wt % to 99.9 wt % of an additive selected from surfactant, solid or liquid diluent, dispersant and adjuvant. The herbicidal composition according to the present invention may be formulated into wettable powder, suspension concentrate, emulsifiable concentrate, emulsion in water, microemulsion, liquid, dispersible liquid, granule, wettable powder, water dispersible granule or tablet.

Typical examples of the herbicidal composition of the present invention are given in Table 2. However, the herbicidal composition of the present invention is not limited thereto.

TABLE 2

| Formulation | Weight proportion (wt %) | | |
|---|---|---|---|
| | Active ingredient | Diluent | Surfactant |
| Wettable powder | 10-90 | 0-80 | 1-10 |
| Suspension concentration | 3-50 | 40-95 | 0-15 |
| Emulsifiable concentrate/ Soluble concentrate | 3-50 | 40-95 | 0-15 |
| Granule | 0.1-95 | 5-98.9 | 1-15 |

The surfactant used in the present invention is an amphiphilic material having high surface activity, with both hydrophilic and lipophilic moieties in the molecule. With superior detergency, dispersibility, emulsifying ability, solubilizing ability, wetting ability, sterilizing ability, foaming ability and penetrating ability, it helps wetting, disintegration, dispersion and emulsification to facilitate effective action of the herbicide. The surfactant may be an anionic surfactant such as a sodium salt or potassium salt of a sulfonate, e.g. alkyl ($C_8$-$C_{12}$) benzenesulfonate, alkyl ($C_3$-$C_6$) naphthalenesulfonate, dialkyl ($C_3$-$C_6$) naphthalenesulfonate, dialkyl ($C_8$-$C_{12}$) sulfosuccinate, lignin sulfonate, naphthalenesulfosuccinate formalin condensate, alkyl ($C_8$-$C_{12}$) naphthalenesulfonate formalin condensate and polyoxyethylene alkyl ($C_8$-$C_{12}$) phenylsulfonate, a sodium salt or potassium salt of a sulfate, e.g. alkyl ($C_8$-$C_{12}$) sulfate, polyoxyethylene alkyl ($C_8$-$C_{12}$) sulfate and polyoxyethylene alkyl ($C_8$-$C_{12}$) phenylsulfate, and a sodium salt or potassium salt of a succinate, e.g. polyoxyalkylene succinate, a non-ionic surfactant such as polyoxyethylene alkyl ($C_8$-$C_{12}$) ether, polyoxyethylene alkyl ($C_8$-$C_{12}$) phenyl ether and polyoxyethylene alkyl ($C_8$-$C_{12}$) phenyl polymer, or a mixture thereof. However, it is not limited to the above-listed examples.

The content of the active ingredient may be varied depending on applications. When occasion demands, the surfactant may be used in higher content than the active ingredient. The surfactant may be added to the active ingredient or mixed with the active ingredient using a tank.

The diluent used in the present invention may be either a solid diluent or a liquid diluent. For a solid diluent, one having a high water-absorbing ability is particularly suited to prepare a wettable powder. For a liquid diluent, one that is stable without phase separation from a solvent even at 0° C. is preferred. The liquid diluent may be water, toluene, xylene, petroleum ether, vegetable oil, acetone, methyl ethyl ketone, cyclohexanone, acid anhydride, acetonitrile, acetophenone, amyl acetate, 2-butanone, butylene carbonate, chlorobenzene, cyclohexane, cyclohexanol, alkyl ester of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, α-pinene, D-limonene, ethyl lactate, ethylene glycol, ethylene glycol butyl ether, ethylene glycol methyl ether, γ-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol and high-molecular-weight alcohol, e.g., amyl alcohol, tetrahydrofurfuryl alcohol, hexanol, octanol, ethylene glycol, propylene glycol and glycerol, N-methyl-2-pyrrolidone, or the like. The solid diluent may be talc, titanium dioxide, agalmatolite clay, silica, attapulgite clay, diatomite, limestone, calcium carbonate, bentonite, calcium montmorillonite, cottonseed hull, wheatmeal, soybean flour, pumice, wood flour, nutshell, lignin, or the like.

A small amount of additive was added to all the formulations in order to prevent foaming, caking, corrosion and bacterial growth.

These compositions can be prepared by a commonly used method. Liquid compositions can be prepared simply mixing the constituents, and fine solid compositions can be prepared by mixed grinding using a hammer mill or a flow mill. Suspensions can be prepared by mixing using a wet mill, and granules can be prepared by spraying the active substance on a granule support.

Typical examples of formulation using the compound of the present invention are as follows.

Formulation Example 1

Wettable Powder

The following components were completely mixed. Subsequently, mixing was carried out while spraying a liquid surfactant on the solid components. The product was ground using a hammer mill to a particle size 100 µm or smaller.
Effective compound, 20 wt %
Dodecylphenol polyethylene glycol ether, 2 wt %
Sodium lignin sulfonate, 4 wt %
Sodium silicon aluminate, 6 wt %
Montmorillonite, 68 wt %

Formulation Example 2

Wettable Powder

The following components were mixed and ground using a hammer mill to a particle size 25 µm or smaller.
Effective compound, 80 wt %
Sodium alkyl naphthalene sulfonate, 2 wt %
Sodium lignin sulfonate, 2 wt %
Synthetic amorphous silica, 3 wt %
Kaolin, 13 wt %

Formulation Example 3

Emulsifiable Concentrate

The following components were mixed and uniformly dissolved to prepare an emulsion.
Effective compound, 30 wt %
Cyclohexanone, 20 wt %
Polyoxyethylene alkyl aryl ether, 11 wt %
Calcium alkylbenzenesulfonic acid, 4 wt %
Methylnaphthalene, 35 wt %

Formulation Example 4

Granule

The following components were uniformly mixed ground. After adding 20 wt % of water to 100 wt % of the mixture, followed by mixing, the mixture was processed into 14-32 mesh granule using an extrusion granulator and then dried.

Effective compound, 5 wt %
Sodium lauryl alcohol sulfuric acid ester salt, 2 wt %
Sodium lignin sulfonate, 5 wt %
Carboxymethyl cellulose, 2 wt %
Potassium sulfate, 16 wt %
Plaster, 70 wt %

For practical use, the formulations according to the present invention were sprayed after being diluted to an adequate concentration.

Uses

The uracil compound according to the present invention exhibits a wide herbicidal effect against not only grass weeds but also broadleaf weeds upon foliar treatment at low concentration. Therefore, it is very useful as a non-selective herbicide for foliar treatment in orchards and non-crop areas. Further, the uracil compound according to the present invention exhibits a good selectivity for crops such as wheat or corn upon soil treatment. Therefore, it is very useful as a herbicide for soil treatment for use in farming of corn and wheat.

The herbicidal composition of the present invention may be used in an amount of 10 g to 1 kg, preferably 10 g to 400 g, per hectare (ha), based on the active ingredient. The amount may be determined considering such factors as the amount of weeds, growth level of the weeds, formulation type, or the like.

The herbicidal composition of the present invention may further comprise, in addition to the compound represented by Formula 1, a commonly used active ingredient having an agrochemical activity as an active ingredient. Known active ingredients that may be used in the herbicidal composition of the present invention may be one or more compound(s) having herbicidal activity selected from the group consisting of acetyl-CoA carboxylase inhibitor (ACC), acetolactate synthase inhibitor (ALS), amide, auxin herbicide, auxin transport inhibitor, carotenoid biosynthesis inhibitor, enolpyruvylshikimate 3-phosphate synthase inhibitor (ESPS), glutamine synthetase inhibitor, lipid biosynthesis inhibitor, mitosis inhibitor, protoporphyrinogen IX oxidase inhibitor, photosynthesis inhibitor, synergist, growth substance, cell wall biosynthesis inhibitor and other herbicide.

The acetyl-CoA carboxylase inhibitor (ACC) may be a cyclohexenone oxime ether such as alloxydim, clethodim, cloproxydim, cycloxydim, sethoxydim, tralkoxydim, butroxydim, clefoxydim or tepraloxydim, or a phenoxyphenoxypropionic acid ester such as metamifop, cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl.

The acetolactate synthase inhibitor (ALS) may be a imidazolinone such as imazapyr, imazaquin, imazamethabenz-methyl, imazamox, imazapic, imazethapyr or imazamethapyr, a pyrimidyl ether such as pyrithiobac-acid, pyrithiobac-sodium, bispyribac-sodium or pyribenzoxym, a sulfonamide such as florasulam, flumetsulam or metosulam, or a sulfonylurea such as amidosulfuron, azimsulfuron, bensulfuron-methyl, chlorimuron-ethyl, chlorsulfuron, chinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, sulfosulfuron, flucetosulfuron or iodosulfuron.

The auxin herbicide may be a pyridinecarboxylic acid such as clopyralid or picloram, 2,4-D or benazolin.

The auxin transport inhibitor may be naptalam or diflufenzopyr, and the carotenoid biosynthesis inhibitor may be benzofenap, clomazone, diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrole.

The enolpyruvylshikimate 3-phosphate synthase inhibitor (ESPS) may be glyphosate or sulfosate, and the glutamine synthetase inhibitor may be bilanafos (bialaphos) or glufosinate-ammonium.

The lipid biosynthesis inhibitor may be an anilide such as anilofos or mefenacet, a chloroacetanilide such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor, a thiourea such as butylate, cycloate, diallate, dimepiperate, EPTC, esprocarb, molinate, pebulate, prosulfocarb, thiobencarb (benthiocarb), triallate or vernolate, benfuresate or perfluidone.

The mitosis inhibitor may be a carbamate such as asulam, carbetamid, chlorpropham, orbencarb, pronamid (propyzamid), propham or thiocarbazil, a dinitroaniline such as benefin, butralin, dinitramin, ethalfluralin, fluchloralin, oryzalin, pendimethalin, prodiamine or trifluralin, a pyridine such as dithiopyr or thiazopyr, butamifos, chlorthal-dimethyl (DCPA) or maleic hydrazide.

The protoporphyrinogen IX oxidase inhibitor may be a diphenyl ether such as acifluorfen, acifluorfen-sodium, aclonifen, bifenox, chlornitrofen (CNP), ethoxyfen, fluorodifen, fluoroglycofen-ethyl, fomesafen, furyloxyfen, lactofen, nitrofen, nitrofluorfen or oxyfluorfen, an oxadiazole such as oxadiargyl or oxadiazon, a cyclic imide such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin, or a pyrazole such as pyraflufen-ethyl.

The photosynthesis inhibitor may be propanil, pyridate or pyridafol, a benzothiadiazinone such as bentazone, a dinitrophenol such as bromofenoxim, dinoseb, dinoseb-acetate, dinoterb or DNOC, a dipyridylene such as cyperquat-chloride, difenzoquat-methylsulfate, diquat or paraquat-dichloride, a urea such as chlorbromuron, chlortoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron, a phenol such as bromoxynil or ioxynil, chloridazon, a triazine such as ametryn, atrazine, cyanazine, desmetryn, dimethamethryn, hexazinone, prometon, prometryn, propazine, simazine, simetryn, terbumeton, terbutryn, terbuthylazine or trietazine, a triazione such as metamitron or metribuzin, a uracil such as bromacil, lenacil or terbacil, or a biscarbamate such as desmedipham or phenmedipham.

The synergist may be an oxirane such as tridiphane, the growth substance may be an aryloxyalkanoic acid such as 2,4-DB, clomeprop, dichlorprop, dichlorprop-P (2,4-DP-P), fluoroxypyr, MCPA, MCPB, mecoprop, mecoprop-P or triclopyr, a benzoic acid such as chloramben or dicamba, or a carboxylic acid such as quinclorac or quinmerac, and the cell wall synthesis inhibitor may be isoxaben or dichlobenil.

The other herbicide may be a dichloropropionic acid such as dalapon, a dihydrobenzofuran such as ethofumesate, a phenylacetic acid such as chlorfenac (fenac), or aziprotryn, barban, bensulide, benzthiazuron, benzofluor, buminafos, buthidazole, buturon, cafenstrole, chlorbufam, chlorfenprop-methyl, chlorxuron, cinmethylin, cumyluron, cycluron, cyprazine, cyprazole, dibenzyluron, dipropetryn, dymron, eglinazine-ethyl, endothall, ethiozin, flucabazone, fluorbentranil, flupoxam, isocarbamid, isopropalin, karbutilate, mefluidid, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon, or an environment-friendly salt thereof.

The compound according to the present invention has remarkable herbicidal activity against harmful monocotyledons (grass weeds) and dicotyledons (broadleaf weeds). Typical weed plants may be controlled by the compound according to the present invention, but they are not limited to particular species.

Specific examples of weed species that may be controlled by the herbicide of the present invention include:

grass weed (monocot) species selected from *Digitaria ciliaris, Agropyron tsukushiense* var. *transiens, Echinochloa crus-galli, Panicum dichotomiflorum, Digitaria violascens, Eleusine indica, Setaria viridis, Setaria viridis* var. *gigantea, Setaria faberi, Leptochloa chinensis, Eragrostis multicaulis, Eragrostis pilosa, Poa sphondylodes, Poa pratensis*, or the like; and broadleaf weed (dicot) species selected from Cyperaceae weeds including *Cyperus amuricus, Cyperus microiria, Cyperus rotundus, Cyperus serotinus, Eleocharis acicularis, Eleocharis kuroguwai, Scirpus fluviatilis*, or the like; Asteraceae weeds including *Eclipta prostrata, Siegesbeckia pubescens, Centipeda minima, Senecio vulgaris, Artemisia princeps* var. *orientalis, Bidens frondosa, Taraxacum officinale, Erigeron annuus, Conyza canadensis, Galinsoga quadriradiata, Hemistepta lyrata, Youngia japonica, Artemisia capillaris, Bidens bipinnata, Siegesbeckia glabrescens, Ambrosia trifida, Ixeris dentata, Youngia sonchifolia, Lactuca indica* var. *laciniata, Aster pilosus, Breea segeta, Taraxacum platycarpum, Ambrosia artemisiifolia* var. *elatior, Helianthus tuberosus, Erechtites hieracifolia*, or the like; Lamiaceae weeds including *Elsholtzia ciliata, Stachys riederi* var. *japonica, Mosla punctulata, Leonurus japonicu*), or the like; Euphorbiaceae weeds including *Acalypha australis, Chamaesyce maculata, Chamaesyce supina*, or the like; Scrophulariaceae weeds including *Mazus pumilus, Lindernia procumbens*, or the like; Solanaceae weeds including *Solanum nigrum, Solanum americanum*, or the like; Amaranthaceae weeds including *Amaranthus lividus, Amaranthus hybridus* var. *patulus*, or the like; Oxalidaceae weeds including *Oxalis corniculata, Oxalis stricta*, or the like; Geraniaceae weeds including *Erodium moschatum, Geranium thunbergii*, or the like; Malvaceae weeds including *Hibiscus trionum, Abutilon theophrasti*, or the like; Cannabinaceae weeds including *Humulus japonicus, Cannabis sativa*, or the like; Onagraceae weeds including *Ludwigia prostrata, Oenothera biennis*, or the like; Portulacaceae weeds including *Portulaca oleracea*, or the like; Equisetaceae weeds including *Equisetum arvense*, or the like; Araceae weeds including *Pinellia ternata*, or the like; Apiaceae weeds including *Torilis japonica*, or the like; Aizoaceae weeds including *Mollugo pentaphylla*, or the like; Commelinaceae weeds including *Commelina communis*, or the like; Crassulaceae weeds including *Sedum sarmentosum*, or the like; Papaveraceae weeds including *Chelidonium majus* var. *asiaticum*, or the like; Asclepiadaceae weeds including *Metaplexis japonica*, or the like; Violaceae weeds including *Viola mandshurica*, or the like; Caryophyllaceae weeds including *Stellaria aquatica*, or the like; Urticaceae weeds including *Pilea mongolica*, or the like; Boraginaceae weeds including *Trigonotis peduncularis*, or the like; Plantaginaceae weeds including *Plantago asiatica*, or the like; Rosaceae weeds including *Potentilla supina*, or the like; etc.

Test Example

Herbicidal effect of the compounds of the present invention was tested as follows.

Test Example

Soil and Foliar Treatment Test

A compound fertilizer for horticulture (N:P:K=11:10:11) was mixed with sterilized sandy soil (pH 6.1, organic substance 1.0%, clay 21%, silt 17%, sand 52%), 1 g per each pot (350 cm$^2$). The soil was filled in a square plastic pot, and corn, Poaceae plants including *Panicum dichotomiflorum* and *Digitaria ciliaris*, broadleaf plants including *Solanum nigrum, Aeschynomene indica, Abutilon theophrasti* and cocklebur, or convolvulus rhizome were sown and covered with soil. Soil treatment was carried out by spraying a test formulation 1 day after the sowing, and foliar treatment, 8 to 12 days after the sowing. The test formulation was prepared by dissolving of a test compound in a mixture of 5 wt % of acetone and 1 wt % of an emulsifier, and diluting with water to prepare a wettable powder. 2000 L of the test formulation was sprayed per hectare. The amount of the active compound was adjusted to a desired quantity.

Following the treatment, the plants were grown for 2 weeks under a greenhouse condition (25-35° C. during the day and 20-25° C. at night, 14 hour light cycle). Herbicidal activity was evaluated in comparison to a non-treated control group according to the following standard: for weeds, 0 (no herbicidal effect) to 100 (complete destruction); and for crops 0 (harmless) to 10 (complete destruction).

The test result is shown in Tables 3 to 7. The compounds represented by Formula 1 exhibited excellent herbicidal activity against broadleaf weeds and grass weeds upon foliar treatment even at low concentrations. Upon soil treatment, they exhibited high selectivity for wheat and corn, and showed powerful herbicidal effect on both broadleaf weeds and grass weeds.

Control compounds were those disclosed in Japanese Patent Laid-Open Nos. 2000-302764 and 2001-172,265, with the following structure:

comparative compound 1

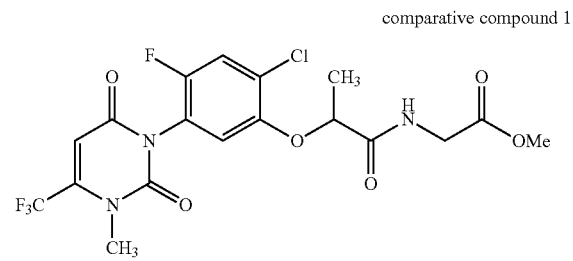

-continued comparative compound 2

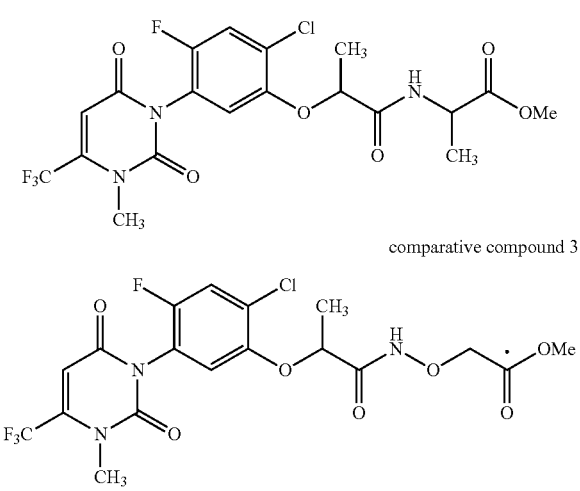

comparative compound 3

TABLE 3

Comparative herbicidal activity test upon foliar treatment (8 g a.i./ha)

| Test substance | Weeds | | |
|---|---|---|---|
| | Grass weeds | | Broadleaf weeds |
| | *Echinochloa crus-galli* | *Digitaria ciliaris* | Cocklebur |
| Comparative compound 1 | 55 | 30 | 98 |
| Comparative compound 2 | 65 | 25 | 70 |
| Comparative compound 3 | 30 | 10 | 95 |
| Compound No. 1 | 100 | 100 | 100 |

TABLE 4

Herbicidal activity test upon foliar treatment (I) (8 g a.i./ha)

| Test substance | Grass weeds | | | Broadleaf weeds | | |
|---|---|---|---|---|---|---|
| | *Cyperus serotinus* | *Digitaria ciliaris* | *Sorghum bicolor* | *Aeschynomene indica* | *Abutilon theophrasti* | Cocklebur |
| Compound No. 1 | 100 | 100 | 97 | 100 | 100 | 100 |
| Compound No. 36 | 100 | 100 | 100 | 100 | 100 | 100 |

TABLE 5

Herbicidal activity test upon foliar treatment (II) (8 g a.i./ha)

| Test substance | Grass weeds | | | Broadleaf weeds | | |
|---|---|---|---|---|---|---|
| | *Echinochloa crus-galli* | *Digitaria ciliaris* | *Panicum dichotomiflorum* | *Solanum nigrum* | *Abutilon theophrasti* | *Aeschynomene indica* |
| Compound No. 1 | 100 | 100 | 100 | 100 | 100 | 100 |
| Compound No. 24 | 98 | 99 | 99 | 100 | 100 | 100 |

TABLE 6

Herbicidal activity test upon foliar treatment (III) (16 g a.i./ha)

| Test substance | Grass weeds | | | Broadleaf weeds | | |
|---|---|---|---|---|---|---|
| | *Echinochloa crus-galli* | *Digitaria ciliaris* | *Panicum dichotomiflorum* | *Solanum nigrum* | *Abutilon theophrasti* | *Aeschynomene indica* |
| Compound No. 22 | 100 | 85 | 100 | 100 | 100 | 100 |
| Compound No. 23 | 100 | 100 | 100 | 100 | 100 | 100 |
| Compound No. 25 | 90 | 100 | 96 | 100 | 100 | 100 |
| Compound No. 26 | 90 | 95 | 90 | 100 | 100 | 100 |

TABLE 7

| | | | grass weeds | | Broadleaf weeds | | |
|---|---|---|---|---|---|---|---|
| Test substance | Crops | | Sorghum bicolor | Digitaria ciliaris | Solanum nigrum | Abutilon theophrasti | Aeschynomene indica |
| | Corn | Wheat | | | | | |
| Compound No. 1 | 2 | 3 | 100 | 100 | 100 | 100 | 100 |
| Compound No. 36 | 0 | 0 | 100 | 100 | 100 | 100 | 100 |

Herbicidal activity test upon soil treatment (32 g a.i./ha)

As seen from the test result, Control compounds 1, 2 and 3 showed imperfect herbicidal activity against cocklebur, and very low herbicidal activity against monocot weeds. Therefore, they need to be treated at high concentrations to control various weeds.

In contrast, the compounds represented by Formula 1, which are amide compounds having a β-amino acid scaffold, exhibited excellent herbicidal activity upon foliar treatment against grass weeds (monocots) and broadleaf weeds (dicots). Therefore, they are useful as a non-selective herbicide for foliar treatment. Further, they exhibited very superior herbicidal activity against grass weeds and broadleaf weeds upon soil treatment, with little harm to the crops. Therefore, they are useful as a selective herbicide for cropping.

Accordingly, the compound represented by Formula 1 may be useful as a highly efficient herbicide, capable of greatly reducing the application rate of the herbicide used and, thereby, avoiding environmental pollutions.

While the present invention has been described with respect to the specific embodiments, it will be apparent to those skilled in the art that various changes and modifications may be made without departing from the spirit and scope of the invention as defined in the following claims.

What is claimed is:

1. A uracil compound represented by Formula 1 or an agrochemically allowable salt thereof:

(1)

wherein $R_1$ and $R_2$, which may be the same or different, represent hydrogen or $C_1$-$C_6$ alkyl;

$R_3$ represents hydrogen, hydroxyl, $C_1$-$C_6$ alkyl, $C_2$-$C_6$ alkenyl, $C_2$-$C_6$ alkynyl, $C_1$-$C_8$ alkoxy, $C_1$-$C_6$ haloalkyl, $C_2$-$C_6$ haloalkenyl, $C_1$-$C_6$ alkoxy $C_1$-$C_6$ alkyl or $C_6$-$C_{10}$ aryl $C_1$-$C_6$ alkoxy;

$R_4$ represents hydrogen, $C_1$-$C_6$ alkyl, $C_1$-$C_6$ haloalkyl or $C_1$-$C_6$ alkoxycarbonyl $C_1$-$C_6$ alkyl;

$R_5$ represents hydrogen, $C_1$-$C_6$ alkyl, $C_1$-$C_6$ alkoxy, $C_2$-$C_6$ haloalkyl, $C_2$-$C_6$ alkenyl, $C_2$-$C_6$ haloalkenyl, $C_2$-$C_6$ alkynyl, $C_1$-$C_6$ alkoxycarbonyl $C_1$-$C_6$ alkyl, $C_6$-$C_{10}$ aryl $C_1$-$C_6$ alkyl or $C_6$-$C_{10}$ aryl $C_1$-$C_6$ alkoxy;

X represents S, SO, or SO2;

Y represents $C_1$-$C_6$ alkylene or $C_1$-$C_6$ haloalkylene; W represents O, S, NH or N($C_1$-$C_6$ alkyl); and Z represents halogen, cyano, $CONH_2$ or $CSNH_2$.

2. The compound according to claim 1, wherein $R_1$ and $R_2$, which may be the same or different, represent hydrogen or methyl;

$R_3$ represents hydrogen, hydroxyl, methyl, ethyl, n-propyl, isopropyl, n-butyl, tert-butyl, vinyl, allyl, methoxy, ethoxy, n-propoxy, n-butoxy, tert-butoxy, chloromethyl, dichloromethyl, fluoromethyl, difluoromethyl, trifluoromethyl or benzyloxy;

$R_4$ represents hydrogen, methyl, ethyl, n-propyl, isopropyl, n-butyl or tert-butyl;

$R_5$ represents hydrogen, hydroxyl, methyl, ethyl, n-propyl, isopropyl, n-butyl, tert-butyl, vinyl, allyl, propargyl, methoxy, ethoxy, n-propoxy, n-butoxy, tert-butoxy, benzyl, phenethyl, methoxycarbonylmethyl, methoxycarbonylethyl, methoxycarbonylpropyl, ethoxycarbonylmethyl, benzyloxy or phenethyloxy;

X represents S, or SO2;

Y represents $CH_2$, $CH(CH_3)$, $CH_2CH_2$, $CH_2CH_2CH_2$, $CH(CF_3)$, $CH(CH_2F)$, $CH(CHF_2)$, $CH_2CHF$ or $CH_2CF_2$;

W represents O, NH or N($CH_3$); and

Z represents chlorine, cyano, $CONH_2$ or $CSNH_2$.

3. The compound according to claim 1, wherein $R_1$ and $R_2$, which may be the same or different, represent hydrogen or methyl;

$R_3$ represents hydrogen, hydroxyl, methyl, methoxy or benzyloxy;

$R_4$ represents hydrogen or methyl;

$R_5$ represents hydrogen, methyl, ethyl, n-propyl, n-butyl, methoxy, allyl, propargyl, benzyl, benzyloxy or methoxycarbonylmethyl;

X represents S, or SO2;

Y represents $CH_2$, $CH(CH_3)$, $CH_2CH_2$, $CH_2CH_2CH_2$ or $CH(CH_2F)$;

W represents O or NH; and

Z represents chlorine, cyano or $CSNH_2$.

4. The compound according to claim 1, which is selected from:

3-[{2-[2-chloro-5-(3,6-dihydro-3-methyl-2,6-dioxo-4-trifluoromethyl-1(2H)-pyrimidinyl)-4-fluorophenylthio]-1-oxopropyl}amino]propionic acid methyl ester (Compound No. 36);

3-[{2-[2-chloro-5-(3,6-dihydro-3 -methyl-2,6-dioxo-4-trifluoromethyl-1(2H)-pyrimidinyl)-4-fluorophenylsulfonyl]-1-oxopropyl}amino]propionic acid methyl ester (Compound No. 61); and an agrochemically allowable salt thereof.

5. A herbicide comprising a uracil compound represented by Formula 1, an agrochemically allowable salt thereof or a mixture thereof as an active ingredient:

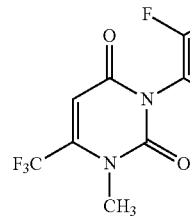

(1)

wherein $R_1$, $R_2$, $R_3$, $R_4$, $R_5$, X, Y, Z and W are the same as defined in claim 1.

6. The herbicide according to claim 5, further comprising an additive, wherein the uracil compound concentration is sufficient to remove grass weeds and broadleaf weeds by foliar application.

7. The herbicide according to claim 5, further comprising an additive, wherein the uracil compound concentration is sufficient to remove grass weeds and broadleaf weeds without damage of crops upon soil treatment.

8. A herbicidal composition comprising:
0.1 wt % to 99.9 wt % of active ingredient selected from the group consisting of a uracil compound represented by Formula 1, an agrochemically allowable salt thereof or a mixture thereof; and
0.1 wt % to 99.9 wt % of an additive selected from a surfactant and a solid or liquid diluent:

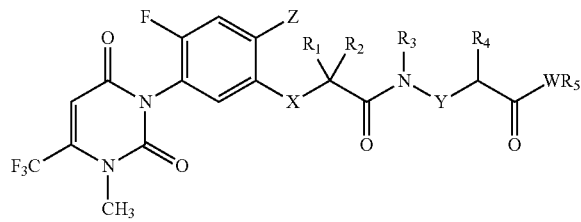

(1)

wherein
$R_1$, $R_2$, $R_3$, $R_4$, $R_5$, X, Y, Z and W are the same as defined in claim 1.

9. The herbicidal composition according to claim 8, which is formulated into a wettable powder, a suspension concentrate, an emulsifiable concentrate, an emulsion oil in water, a microemulsion, a soluble concentrate, a dispersible liquid, a water dispersible granule, a granule or a tablet.

10. The herbicidal composition according to claim 8, wherein the active ingredient further comprises one or more selected from the group consisting of acetyl-CoA carboxylase inhibitor (ACC), acetolactate synthase, inhibitor (ALS), amide, auxin herbicide, auxin transport inhibitor, carotenoid biosynthesis inhibitor, enolpyruvylshikimate 3-phosphate synthase inhibitor (ESPS), glutamine synthetase inhibitor, lipid biosynthesis inhibitor, mitosis inhibitor, protoporphyrinogen IX oxidase inhibitor, photosynthesis inhibitor, synergist, growth substance, cell wall biosynthesis inhibitor and known herbicide.

* * * * *